(12) United States Patent
Hirata et al.

(10) Patent No.: US 12,202,134 B2
(45) Date of Patent: Jan. 21, 2025

(54) BENDING OPERATION MECHANISM

(71) Applicant: NHK SPRING CO., LTD., Kanagawa (JP)

(72) Inventors: Takafumi Hirata, Kanagawa (JP); Yuki Hotoda, Kanagawa (JP); Masahiro Inaba, Kanagawa (JP)

(73) Assignee: NHK SPRING CO., LTD., Kanagawa (JP)

( * ) Notice: Subject to any disclaimer, the term of this patent is extended or adjusted under 35 U.S.C. 154(b) by 0 days.

(21) Appl. No.: 18/034,360

(22) PCT Filed: Oct. 29, 2021

(86) PCT No.: PCT/JP2021/040035
§ 371 (c)(1),
(2) Date: Apr. 27, 2023

(87) PCT Pub. No.: WO2022/092267
PCT Pub. Date: May 5, 2022

(65) Prior Publication Data
US 2023/0405844 A1 Dec. 21, 2023

(30) Foreign Application Priority Data
Oct. 30, 2020 (JP) ................. 2020-183191

(51) Int. Cl.
*B25J 18/06* (2006.01)
(52) U.S. Cl.
CPC .................... *B25J 18/06* (2013.01)

(58) Field of Classification Search
CPC ..... B25J 18/06; B25J 9/06; B25J 9/104; B25J 3/02; A61B 2034/301; A61B 2034/305;
(Continued)

(56) References Cited

U.S. PATENT DOCUMENTS 2,998,242 A * 8/1961 Schwarzbeck .......... F16F 1/042
267/204
7,364,582 B2 4/2008 Lee
(Continued)

FOREIGN PATENT DOCUMENTS

| CN | 110269694 | 9/2019 |
|---|---|---|
| JP | 2020026019 | 2/2020 |

(Continued)

OTHER PUBLICATIONS

English Translation of WO2019073859A1 (Year: 2019).*
(Continued)

*Primary Examiner* — Victor L MacArthur
(74) *Attorney, Agent, or Firm* — JCIPRNET

(57) ABSTRACT

A bending operation mechanism comprises: an elastically bendable driving part; an elastically bendable driven part that is provided separate from the driving part; and a linking part that connects the driving part and the driven part, and tensions and bends the driven part in accordance with bending of the driving part. The driving part and the driven part each comprise an inner coil part and an outer coil part that are bendable with respect to the axial direction, and wound parts corresponding to the inner coil part are respectively fitted to pitches between adjacent wound parts of the outer coil part.

11 Claims, 12 Drawing Sheets

(58) Field of Classification Search
CPC ..... A61B 1/0057; A61B 1/0055; A61B 34/30; A61B 2017/00323; A61B 2017/00305; A61B 2017/2905; A61M 25/0138; A61M 25/0147
See application file for complete search history.

(56) References Cited

U.S. PATENT DOCUMENTS

| | | | |
|---|---|---|---|
| 7,410,483 B2 * | 8/2008 | Danitz | A61B 17/072 606/1 |
| 8,398,587 B2 * | 3/2013 | Dewaele | A61B 34/70 600/101 |
| 2005/0107667 A1 | 5/2005 | Danitz et al. | |
| 2010/0191278 A1 | 7/2010 | Lee et al. | |
| 2017/0234411 A1 * | 8/2017 | Dewaele | A61B 17/00234 74/479.01 |

FOREIGN PATENT DOCUMENTS

| | | | |
|---|---|---|---|
| WO | 2015105421 | 7/2015 | |
| WO | WO-2019073859 A1 * | 4/2019 | A61B 17/29 |

OTHER PUBLICATIONS

"International Preliminary Report On Patentability of PCT/JP2021/040035; this report contains the following items: Form PCT/IB/326, PCT/IB/338, PCT/IB/373, PCT/ISA237(cover sheet), PCT/ISA237(Box No. I), PCT/ISA237(Box No. V)", mailed on May 11, 2023, which is English translation of "Written Opinion of the International Searching Authority", p. 1-p. 9.

"International Search Report (Form PCT/ISA/210) of PCT/JP2021/040035", mailed on Jan. 11, 2022, with English translation thereof, pp. 1-4.

"Office Action of Taiwan Counterpart Application", issued on May 10, 2022, with English translation thereof, pp. 1-14.

"Office Action of Taiwan Counterpart Application", issued on Dec. 2, 2022, with English translation thereof, pp. 1-8.

"Search Report of Europe Counterpart Application", issued on Apr. 4, 2024, pp. 1-9.

* cited by examiner

BENDING OPERATION MECHANISM

CROSS-REFERENCE TO RELATED APPLICATION

This application is a 371 application of the International PCT application serial no. PCT/JP2021/040035, filed on Oct. 29, 2021, which claims the priority benefits of Japan Patent Application No. 2020-183191, filed on Oct. 30, 2020. The entirety of each of the above-mentioned patent applications is hereby incorporated by reference herein and made a part of this specification.

TECHNICAL FIELD

The invention relates to a bending operation mechanism provided for joint function parts such as robots and manipulators.

BACKGROUND TECHNOLOGY

Some robots, manipulators, or actuators have joint function parts that enable bending and extension. A bending operation mechanism for operating such a joint function part is described in Patent Literature 1.

The bending operation mechanism of Patent Literature 1 has a first part that is a driving part and a second part that is a driven part. The first part and the second part have an elastic structure constructed by stretching the ends of a plurality of cables at both ends.

In this bending operation mechanism, the cable is pulled by bending the first part, and the second part is bent by being driven. Therefore, the second part is driven and follows the first part, and an intuitive operation becomes possible.

However, in such a bending operation mechanism, the first part can be pushed in the axial direction, so if the first part is pushed in and bent, the followability of the second part decreases, resulting in the decrease of intuitiveness and operational accuracy.

CITATION LIST

Patent Literature

[Patent Literature 1]: International Publication No. 2015/105421

SUMMARY OF THE INVENTION

Technical Problem

The problem of the decreasing followability of the driven part to the driving part needs to be solved.

Solution to Problem

The invention provides a bending operation mechanism, including: a driving part that is elastically bendable; a driven part that is spaced apart from the driving part and is elastically bendable; and a linking part that connects between the driving part and the driven part and pulls and bends the driven part in response to bending of the driving part. Each of the driving part and the driven part includes an inner coil part and an outer coil part that are bendable in an axial direction, and wound parts corresponding to the inner coil part are fitted to gaps between adjacent wound parts of the outer coil part.

Effects of Invention

According to the invention, the corresponding wound parts of the inner coil part fit into the gaps between the adjacent wound parts of the outer coil part, so that the driving part and the driven part are prevented from being pushed in the axial direction, and the followability of the driven part to the driving part may be improved.

Figure 2:
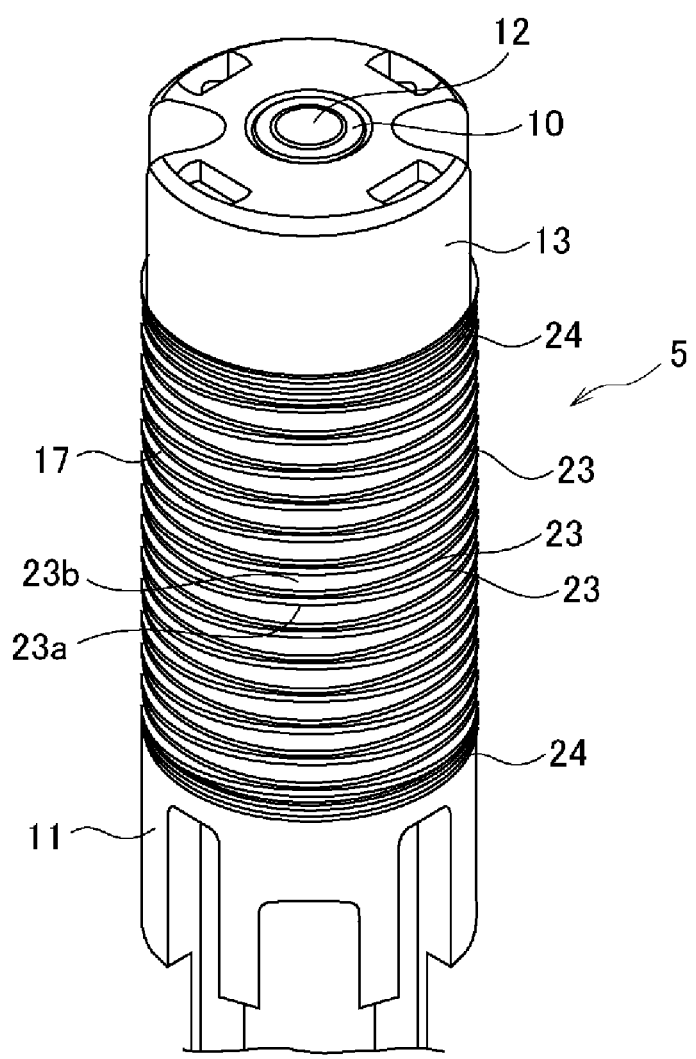
FIG. 2 is an enlarged perspective view of a driving part of the bending operation mechanism of FIG. 1.
Figure 4:
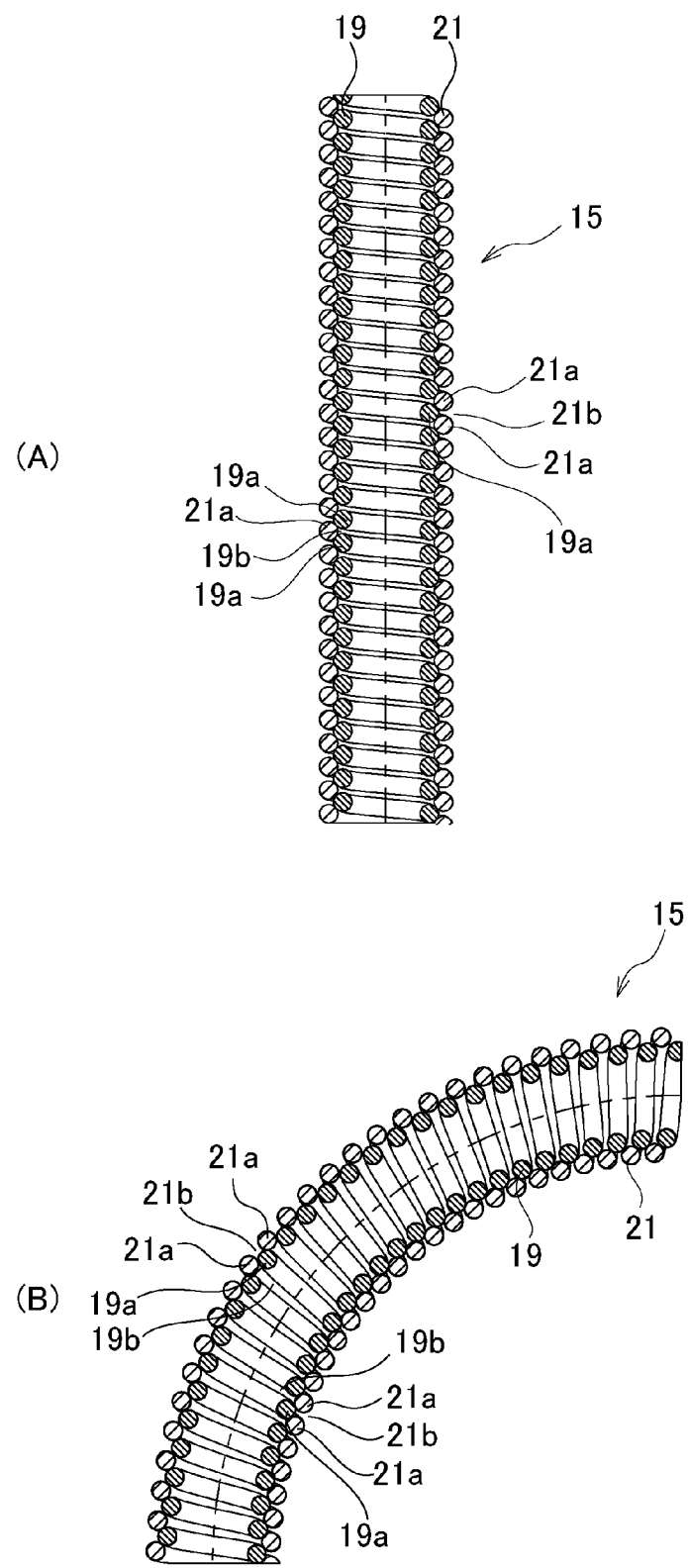

(A) and (B) of FIG. 4 are cross-sectional views showing an inner cylinder used in the driving part of FIG. 2. (A) of FIG. 4 shows a normal state and (B) of FIG. 4 shows a bending state.

Figure 1:
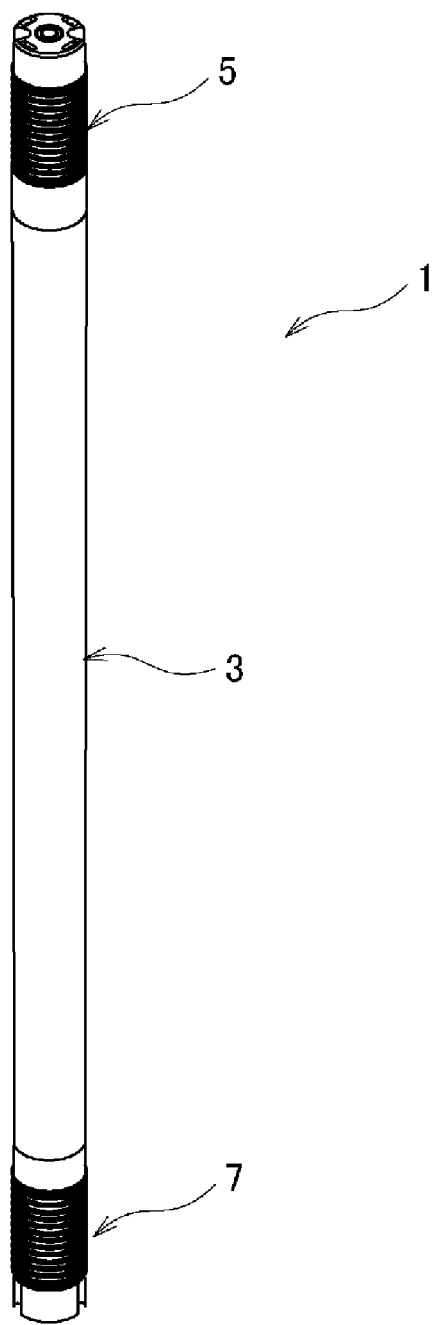
FIG. 1 is a perspective view showing a bending operation mechanism according to example 1 of the invention.
Figure 5:
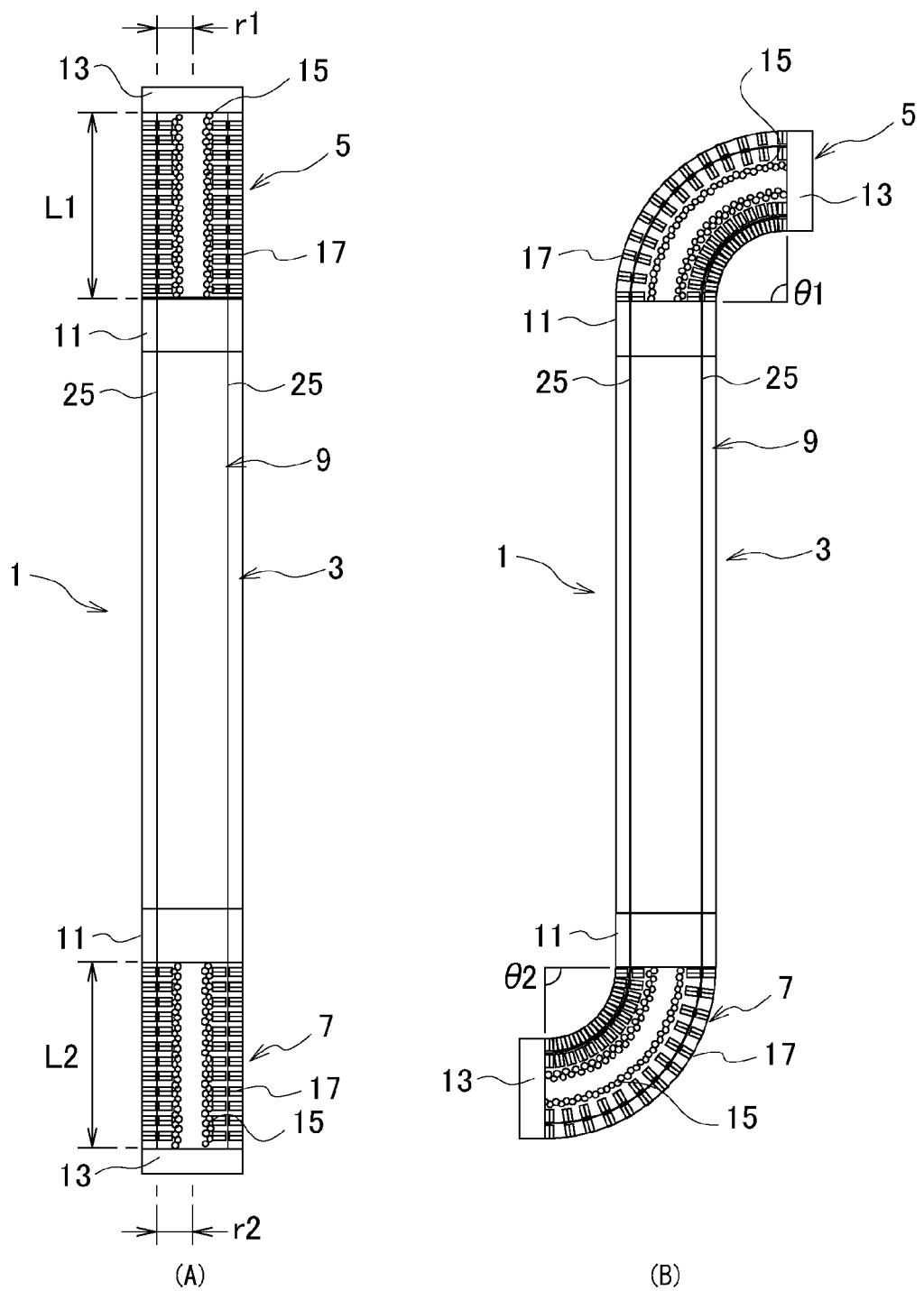

(A) and (B) of FIG. 5 are schematic cross-sectional views of the bending operation mechanism of FIG. 1. (A) of FIG. 5 shows a normal state and (B) of FIG. 5 shows a bending state.

Figure 6:
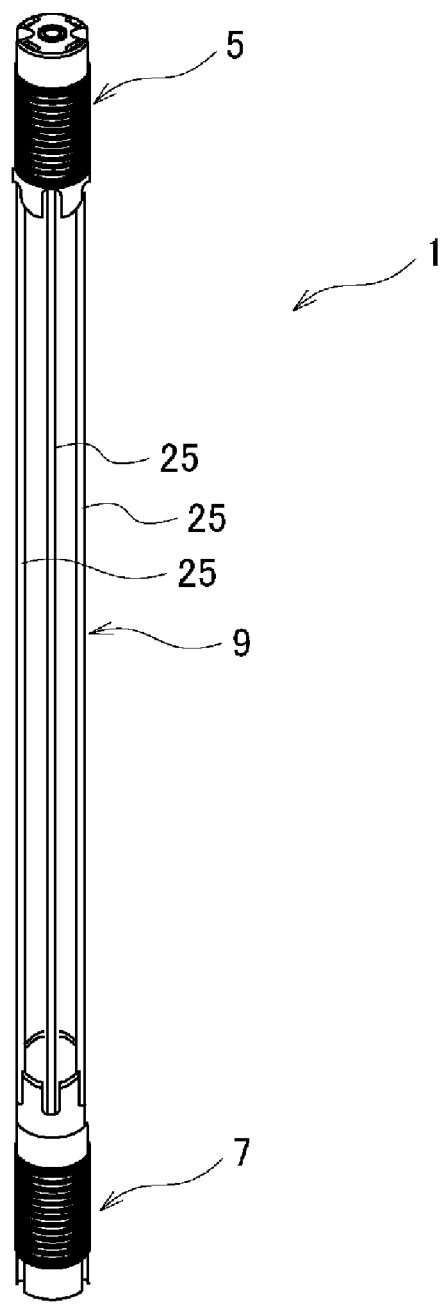

FIG. 6 is a perspective view showing a state of a drive wire of the bending operation mechanism of FIG. 1.

Figure 7:
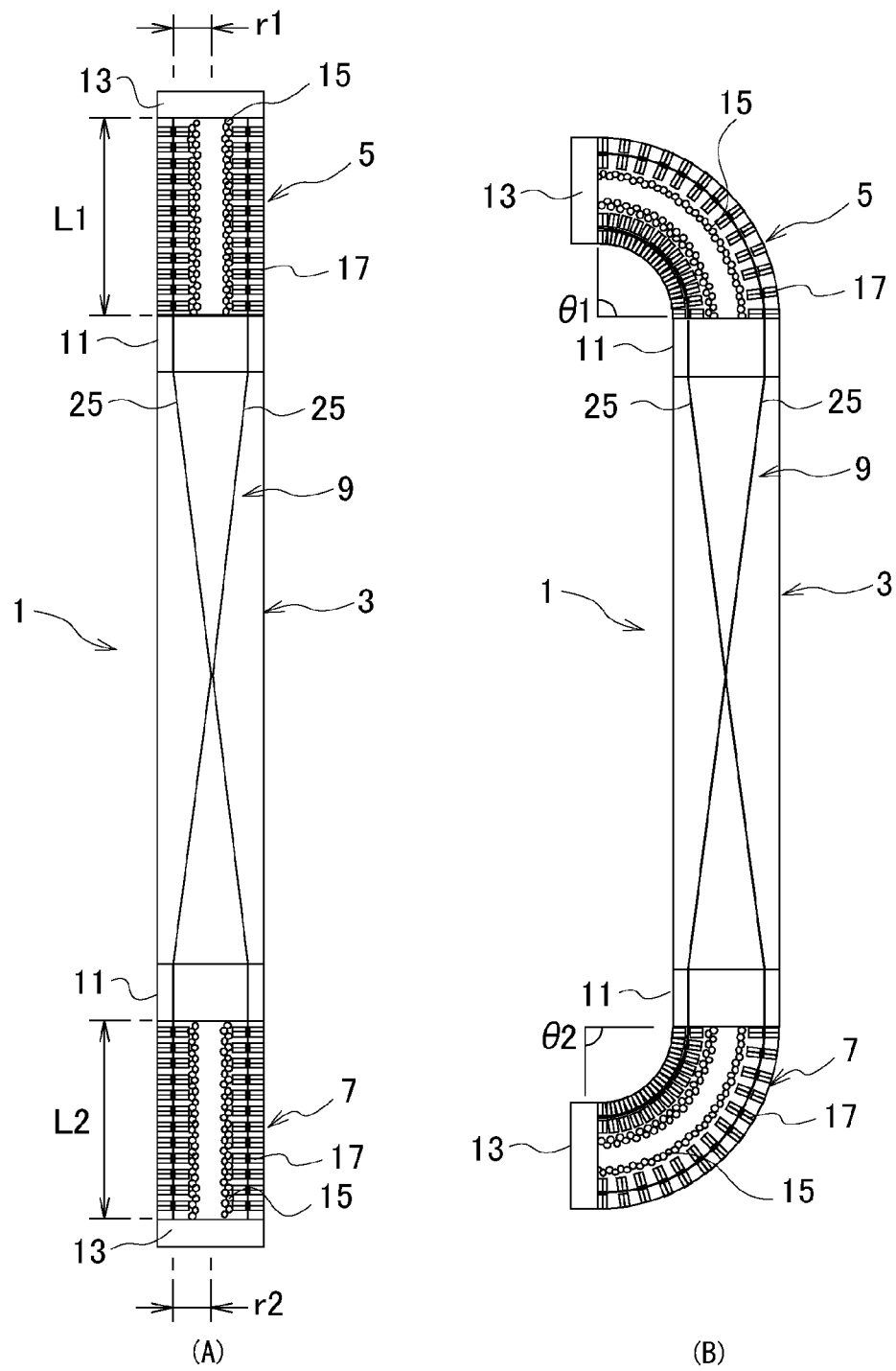

(A) and (B) of FIG. 7 are schematic cross-sectional views of a bending operation mechanism according to example 2 of the invention. (A) of FIG. 7 shows a normal state and (b) of FIG. 7 shows a bending state.

Figure 8:
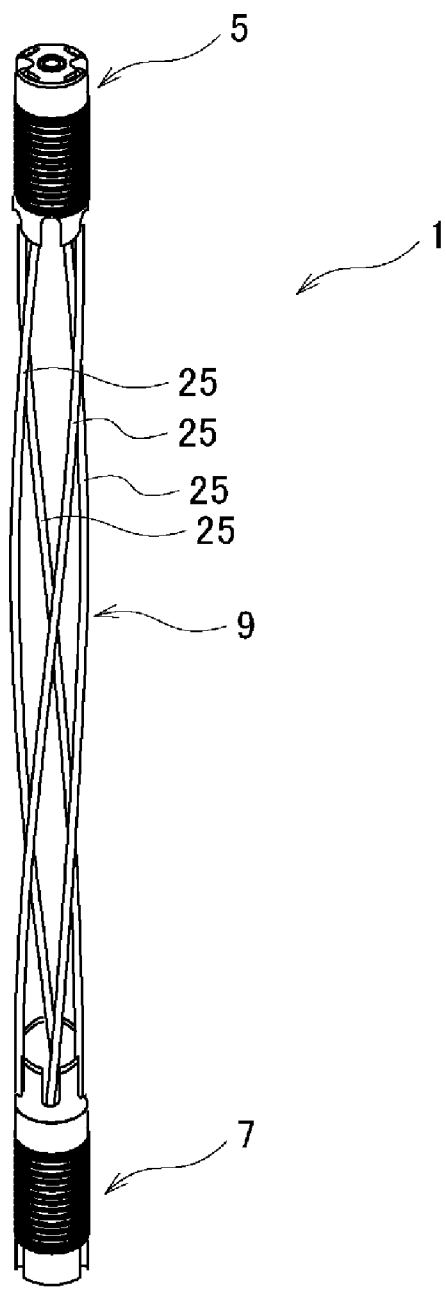

FIG. 8 is a perspective view showing a state of a drive wire of the bending operation mechanism of FIG. 7.

Figure 9:
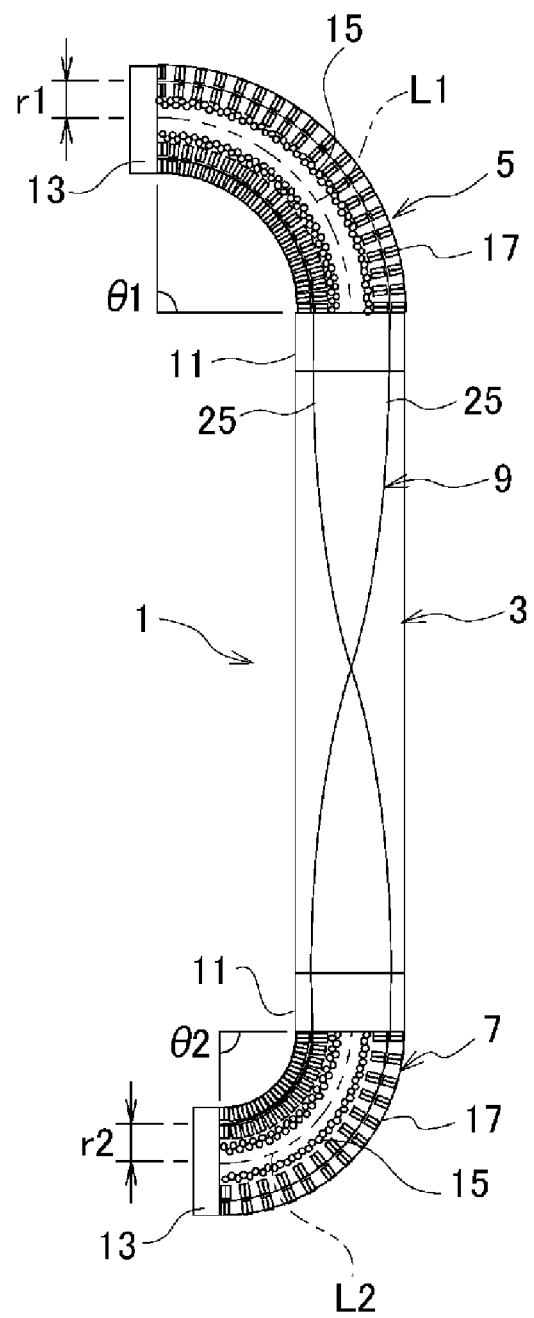

FIG. 9 is a schematic cross-sectional view showing a bending operation mechanism according to example 3 of the invention when bent.

Figure 10:
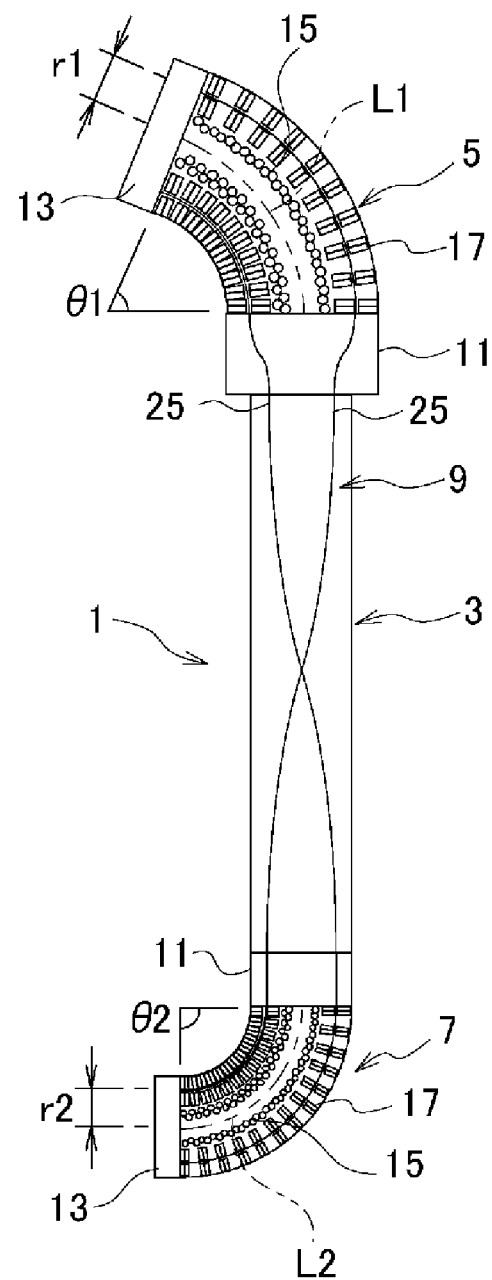

FIG. 10 is a schematic cross-sectional view showing a bending operation mechanism according to example 4 of the invention when bent.

Figure 11:
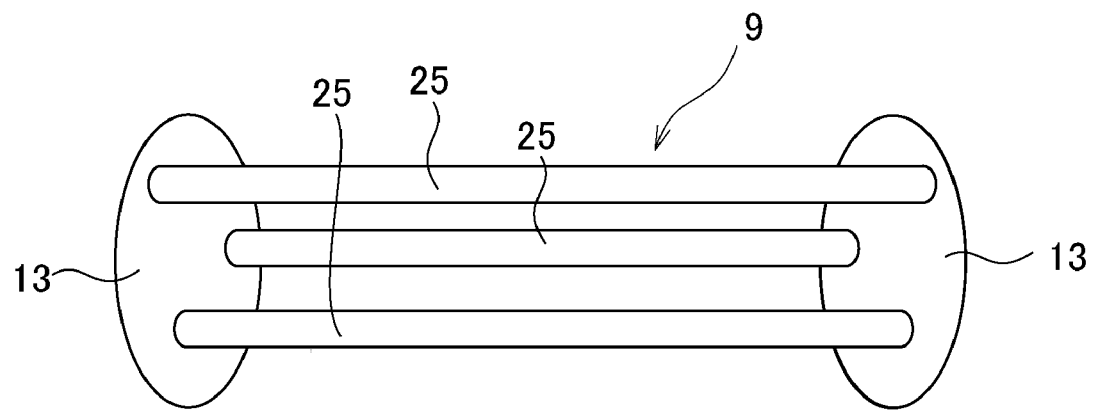

FIG. 11 is a schematic view showing a state of a drive wire of a bending operation mechanism according to example 5 of the invention.

Figure 12:
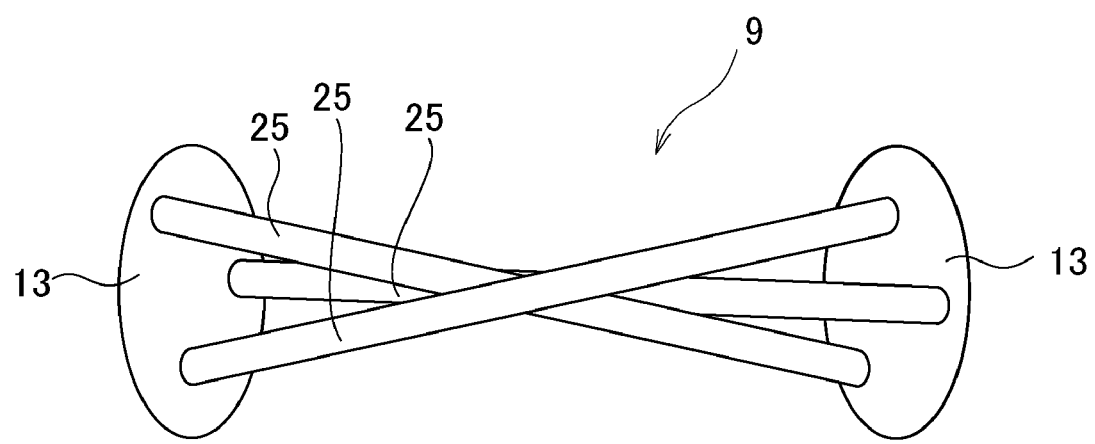

FIG. 12 is a schematic view showing a state of a drive wire of a bending operation mechanism according to a modification of the example 5 of the invention.

Figure 13:
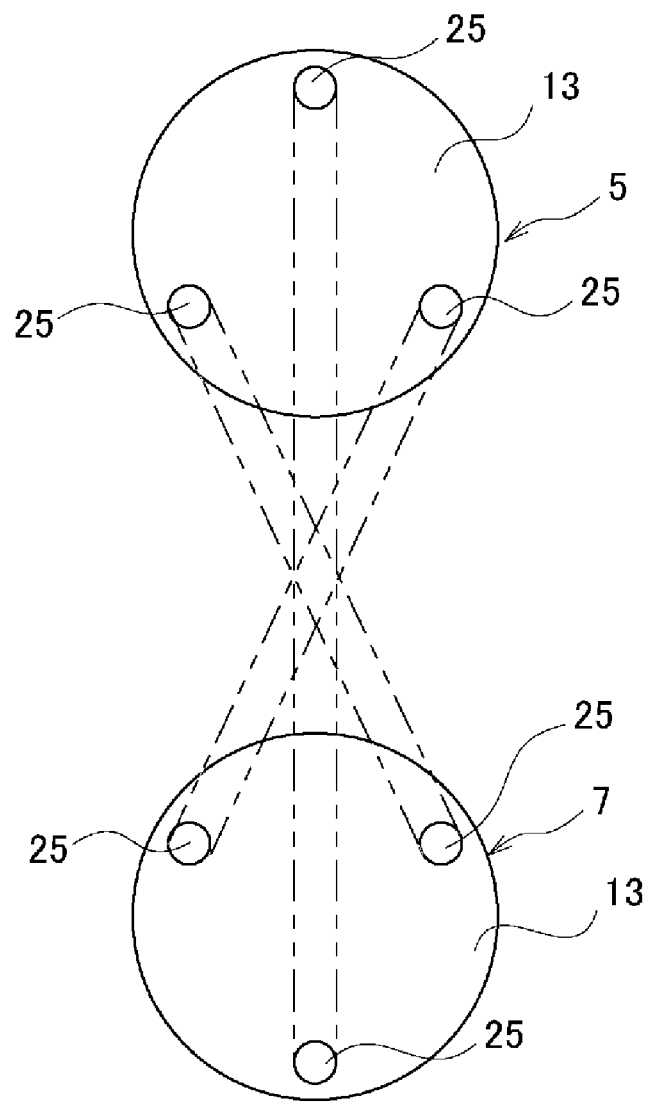

FIG. 13 is a conceptual view showing the connection positional relationship of the drive wires of the bending operation mechanism of FIG. 12.

DESCRIPTION OF EMBODIMENTS

The purpose of improving the followability of the driven part to the driving part was achieved by using double coils for the driving part and the movable part.

That is, the bending operation mechanism (1) includes a driving part (5), a driven part (7), and a linking part (9). The driving part (5) is elastically bendable, and the driven part (7) is provided apart from the driving part (5) and is elastically bendable. The linking part (9) connects between the driving part (5) and the driven part (7), and pulls and bends the driven part (7) according to the bending of the driving part (5).

Each of the driving part (5) and the driven part (7) includes an inner coil part (19) and an outer coil part (21) that are bendable in the axial direction, and corresponding wound parts (19a) of the inner coil part (19) are fitted in the pitches (21b) in adjacent wound parts (21a) of the outer coil part (21).

The length (L1) from the connection position of the linking part (9) with respect to the driving part (5) to the base end part (13) of the driving part (5) are allowable to be different from the length (L2) from the connection position of the linking part (9) with respect to the driven part (7) to the base end part (13) of the driven part (7).

In this case, the driving part (5) and the driven part (7) have different lengths in the axial direction, and the linking part (9) may connect the tip parts (11) of the driving part (5) and the driven part (7).

The linking part (9) is a cord-like member (25) that connects positions radially displaced from the center of the driving part (5) and the driven part (7). When $\theta1$ is the bending angle of the driving part (5), $\theta2$ is the bending angle of the driven part (7), r1 is the amount of displacement of the cord-like member (25) at the driving part (5), and r2 is the amount of displacement of the cord-like member (25) at the driven part (7), there is a relationship of $\theta1:\theta2=r2:r1$.

The linking part (9) includes one or more cord-like members (25), and each cord-like member (25) may connect the driving part (5) and the driven part (7) at positions different by 180 degrees in the circumferential direction.

Each cord-like member (25) is helically formed between the driving part (5) and the driven part (7) and the spiral shape between the driving part (5) and the driven part (7) causes the cord-like members (25) to be displaced by 180 degrees corresponding to the connection at the positions differing by 180 degrees.

Example 1

[Bending Operation Mechanism]

Figure 3:
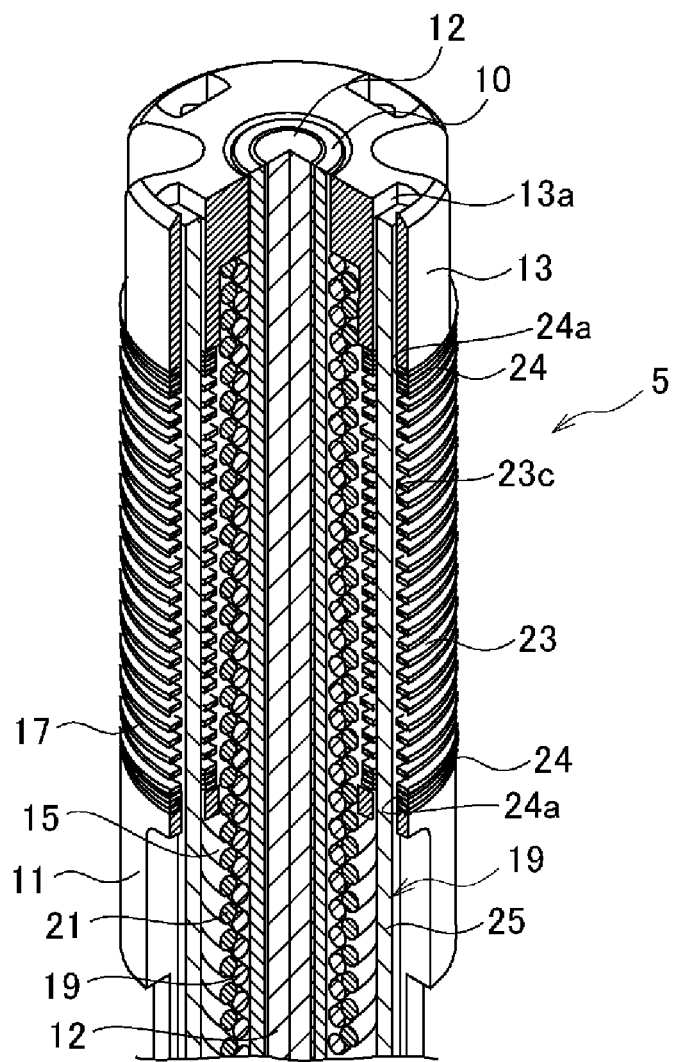
FIG. 3 is a perspective cross-sectional view of a part of the driving part in FIG. 2.

FIG. 1 is a perspective view showing a bending operation mechanism according to example 1 of the invention. FIG. 2 is an enlarged perspective view of a driving part of the bending operation mechanism. FIG. 3 is a perspective cross-sectional view of a part of the driving part. (A) and (B) of FIG. 4 are cross-sectional views showing an inner cylinder used in the driving part, (A) of FIG. 4 shows a normal state, and (B) of FIG. 4 shows a bending state. (A) and (B) of FIG. 5 are schematic cross-sectional views of the bending operation mechanism, (A) of FIG. 5 shows a normal state, and (B) of FIG. 5 shows a bending state. FIG. 6 is a perspective view showing the state of the drive wire of the bending operation mechanism.

The bending operation mechanism 1 is applied to joint function parts of various devices such as manipulators, robots, and actuators for medical and industrial purposes. A joint function part is an apparatus, a mechanism, a device or the like, with the functions as a joint that bends and extends.

The bending operation mechanism 1 of this example includes a shaft 3, a driving part 5, a driven part 7, a linking part 9, a flexible tube 10 as a flexible member, and a push-pull cable 12.

The shaft 3 has a hollow tubular shape formed by metal or the like, for example, a cylindrical shape. A driving part 5 and a driven part 7 are provided at both ends of the shaft 3. The shaft 3 thus functions as a base on which the driving part 5 and the driven part 7 are provided. For the base of the driving part 5 and the driven part 7, an appropriate member may be used instead of the shaft 3 according to the equipment to which the bending operation mechanism 1 is applied.

The driving part 5 is coaxially provided at one end of the shaft 3 and configured to be elastically bendable in the axial direction. The axial direction means a direction along the axial center of the bending operation mechanism 1, and includes directions strictly parallel to the axial center as well as slightly inclined directions.

The driving part 5 is a part that is directly or indirectly operated by the operator, and performs a bending motion according to the operation. The driving part 5 of this example includes a base part 11, a movable part 13, an inner cylinder 15, and an outer cylinder 17.

The base part 11 is a columnar body, such as a circular columnar body, made of resin, metal or the like. The base part 11 is attached to one end of the shaft 3 and constitutes the base end part of the driving part 5. Note that the base part 11 is not limited to a columnar body, and may be formed in an appropriate form according to the equipment to which the bending operation mechanism 1 is applied.

The movable part 13 is, like the base part 11, a columnar body, such as a circular columnar body, made of resin, metal or the like. The movable part 13 constitutes the tip part of the driving part 5. Note that the movable part 13 also has an appropriate form according to the equipment to which the bending operation mechanism 1 is applied, and is not limited to a columnar body.

The movable part 13 is supported by the base part 11 that is displaceable in the axial direction by the inner cylinder 15 and the outer cylinder 17.

The inner cylinder 15 is arranged along the axial direction of the driving part 5. The inner cylinder 15 is a double coil that is able to be elastically bent and restored in the axial direction, and includes an inner coil part 19 and an outer coil part 21.

The inner coil part 19 and the outer coil part 21 are each made of metal, resin or the like, and are elastic coil springs that are bendable in the axial direction. The cross-sectional shape of the wires of the inner coil part 19 and the outer coil part 21 is circular. However, the cross-sectional shape is not limited to a circle, and may be a semicircle, an ellipse or the like.

The inner coil part 19 has a smaller center diameter than the outer coil part 21 and is screwed into the outer coil part 21. The center diameters of the inner coil part 19 and the outer coil part 21 are constant from one end to the other end in the axial direction. However, the center diameter of the outer coil part 21 may also be changed in the axial direction.

The outer coil part 21 has pitches 21b, which are a plurality of gaps separating between axially adjacent wound parts 21a (adjacent wound parts 21a) in the axial direction. Corresponding wound parts 19a of the inner coil part 19 are fitted into the plurality of pitches 21b from the inside. Due to this fitting, the wound parts 19a of the inner coil part 19 contact both the adjacent wound parts 21a of the outer coil part 21.

On the other hand, the inner coil part 19 has pitches 19b as a plurality of gaps separating between axially adjacent wound parts 19a (between wound parts 19a) in the axial direction. Corresponding wound parts 21a of the outer coil part 21 are fitted into the plurality of pitches 19b from the outside. Due to this fitting, the wound parts 21a of the outer coil part 21 contact both the adjacent wound parts 19a of the inner coil part 19.

With such a configuration, the inner cylinder 15 is restricted from being compressed in the axial direction.

The outer cylinder 17 is a cylindrical body arranged concentrically with the inner cylinder 15 and covering the outer circumference of the inner cylinder 15. The outer cylinder 17 of this example is constructed by laminating a plurality of wave washers 23 in the axial direction. Axially adjacent wave washers 23 are joined together. This outer cylinder 17 is bendable by elastic deformation of the wave washers 23.

Each wave washer 23 is formed in a closed ring from metal, resin or the like. Between the wave washers 23 adjacent in the axial direction, the ridge 23a of one wave washer 23 abuts against the trough 23b of the other wave washer 23, and the abutting ridges 23a and troughs 23b are joined by any suitable means such as welding or bonding.

A plurality of flat washers 24 having a smaller deformation amount than the wave washers 23 are attached to both ends of the outer cylinder 17 in the axial direction. The base part 11 and the movable part 13 are connected to both ends of the outer cylinder 17 via the flat washers 24. This connection is made by suitable means such as welding. Note that the flat washer 24 may be omitted.

The outer cylinder 17 is provided with insertion holes 23c and 24a communicating in the axial direction between the ridges 23a and the troughs 23b of each wave washer 23 and at the part of the flat washer 24 corresponding thereto. The insertion holes 23c and 24a of this example are provided at intervals of 90 degrees in the circumferential direction.

The drive wire 25 of the linking part 9 is axially inserted through the insertion holes 23c and 24a. Thereby, the outer cylinder 17 functions as a guide that holds the drive wire 25 at a predetermined position.

It should be noted that the outer cylinder 17 is not limited to the one in which the wave washers 23 are laminated, and may be configured by other flexible members. For example, the outer cylinder 17 may be composed of a bellows made of a tubular body having a corrugated cross section or a double coil similar to the inner cylinder 15.

The driven part 7 is coaxially provided at the other end of the shaft 3 and is provided apart from the driving part 5. The driven part 7 constitutes a joint function part of a device to which the bending operation mechanism 1 is applied, and is configured to be elastically bendable in the axial direction. The bending of the driven part 7 is performed by following the bending of the driving part 5.

The driven part 7 of this example has the same structure as the driving part 5 and is composed of a base part 11, a movable part 13, an inner cylinder 15 and an outer cylinder 17. Therefore, each part of the driven part 7 may be referred to by replacing the description of the driving part 5 with the driven part 7.

Note that the driven part 7 is configured in the opposite direction to the driving part 5. Therefore, the bending direction of the driven part 7 is opposite to the bending direction of the driving part 5. The movable part 13 of the driven part 7 constitutes a tip part of the driven part 7, and an end effector or the like is attached thereto according to the equipment to which the bending operation mechanism 1 is applied.

The linking part 9 connects between the driving part 5 and the driven part 7 and pulls and bends the driven part 7 according to the bending of the driving part 5. The linking part 9 includes a plurality of mutually parallel drive wires 25 as one or more cord-like members. In this example, four drive wires 25 are provided.

Each drive wire 25 is a cord-like member made of metal or the like. The drive wire 25 has a degree of flexibility that does not hinder bending and restoration of the driving part 5 and the driven part 7 of the bending operation mechanism 1.

The cross-sectional shape of the drive wire 25 may be circular like the insertion holes 23c and 24a of the outer cylinder 17, or may be oval or rectangular. Further, the drive wire 25 may be a stranded wire, a NiTi (nickel titanium) single wire, a piano wire, an articulated rod, a chain, a cord, a thread, a rope or the like, as long as the drive wire 25 is a cord-like member.

The drive wire 25 is axially inserted through the shaft 3, the driving part 5, and the driven part 7. In the driving part 5 and the driven part 7, the drive wire 25 is inserted through the insertion holes 23c and 24a of the outer cylinder 17 and guided. Inside the shaft 3, the drive wire 25 is guided by a guide member not shown. The guide member is a plate or the like fixed inside the shaft 3, and may have an insertion hole, a slit, or the like through which the drive wire 25 is inserted.

According to this guide, the drive wire 25 extends axially at a position radially displaced from the centers of the driving part 5, the driven part 7, and the shaft 3 when the bending operation mechanism 1 is straight (extended).

Both ends of the drive wire 25 are connected to positions displaced in the radial direction from the center of the movable part 13 as the tip parts of the driving part 5 and the driven part 7 according to the guide of the drive wire 25. Thus, the drive wire 25 as the linking part 9 is configured to connect the positions displaced in the radial direction from the centers of the driving part 5 and the driven part 7.

In this example, the amount of displacement r1 of the drive wire 25 at the driving part 5 is equal to the amount of displacement r2 of the drive wire 25 at the driven part 7. Although the drive wire 25 connects between the movable parts 13 of the driving part 5 and the driven part 7 under tension, the tension of the drive wire 25 may be appropriately set according to the characteristics or the like of the bending operation mechanism 1.

Both ends of the drive wire 25 are positioned in connection holes 13a provided in the movable part 13, and are prevented from coming off by being engaged with the movable part 13 by end processing or the like. Both ends of the drive wire 25 are thereby connected to the driving part and the driven part 7.

Therefore, in the drive wire 25 of this example, the engagement positions with the movable parts 13 on both sides are the connection positions of the linking part 9 with the driving part 5 and the driven part 7. The connection positions are axial positions corresponding to each other, and are symmetrical with respect to a radial line passing through the center of the bending operation mechanism 1 in the axial direction in this example. The connection may be made by an appropriate technique such as welding or adhesion, and the connection position may be set according to the connection technique.

The length L1 from the connection position of the linking part 9 to the driving part 5 to the base part 11 as the base end part of the driving part 5 is the same as the length L2 from the connection position of the linking part 9 to the driven part 7 to the base part 11 as the base end part of the driven part 7.

The length L1 is the length from the connection position of the linking part 9 to the driving part 5 to an arbitrary axial position of the base part 11 of the driving part 5. Similarly, the length L2 is the length from the connection position of the linking part 9 to the driven part 7 to an arbitrary axial position of the base part 11 of the driven part 7. The arbitrary axial positions of the base part 11 are axial positions corresponding to each other, and in this example, mean symmetrical positions with respect to a line passing through the axial center of the bending operation mechanism 1 along the radial direction.

Since the amounts of displacement r1 and r2 are equal as described above, in this example, the bending angle θ1 when the driving part 5 is bent is equal to the bending angle θ2 of the driven part 7 bent following the driving part 5. The relationship between the length bending angles θ1 and θ2 and the amounts of displacement r1 and r2 is θ1:θ2=r2:r1. In addition, the bending angle refers to the central angle of the axial center of the inner cylinder 15 and the outer cylinder 17 which are responsible for the bending motion.

The flexible tube 10 is positioned at the axial center part of the bending operation mechanism 1 and is a cylindrical member made of resin or the like. Both ends of the flexible tube 10 are inserted through the inner cylinders 15 of the driving part 5 and the driven part 7. This flexible tube 10 has a degree of flexibility that does not hinder the bending and restoration of the driving part 5 and the driven part 7.

The push-pull cable 12 is inserted through the flexible tube 10. The push-pull cable 12 operates an end effector or the like by advancing and retreating.

Depending on the device, it is possible to use a drive member such as an air tube other than the push-pull cable 12, or another member having flexibility. Also, depending on the device, either one or both of the flexible members of the flexible tube 10 and the push-pull cable 12 may be omitted.

[Motion]

In the bending operation mechanism 1 of this example shown in (A) of FIG. 4 and (A) of FIG. 5, when in a straight (extended) state where the driving part 5 and the driven part 7 are not bent, the corresponding wound parts 19a of the inner coil part 19 are fitted between adjacent wound parts 21a of the outer coil part 21 of the inner cylinder 15 in the driving part 5 and the driven part 7.

Therefore, in the bending operation mechanism 1, the inner and outer coil parts 19 and 21 of the inner cylinder 15 are not compressed even if a compressive force in the axial direction acts on the driving part 5 or the driven part 7. As a result, the driving part 5 and the driven part 7 are not pushed in, and the length of the central part is able to be maintained.

Therefore, before the operator bends the driving part 5, the driving part 5 and the driven part 7 are prevented from being pushed inadvertently, and the lengths of the central parts of the driving part 5 and the driven part 7 are prevented from fluctuating.

In this bending operation mechanism 1, when bending the driven part 7, the operator bends the driving part 5 in any direction in all directions of 360 degrees. As a result, any one or a plurality of drive wires 25 are pulled, and the driven part 7 is pulled and driven to be bent. Therefore, the end effector or the like of the equipment to which the bending operation mechanism 1 is applied is able to be oriented in a desired direction.

When the drive wire 25 is pulled, as shown in (B) of FIG. 4 and (B) of FIG. 5, the pitches 21b between the adjacent wound parts 21a of the outer coil part 21 of the inner cylinder 15 becomes smaller on the inner side of the bend, and the pitches 21b between the adjacent wound parts 21a of the outer coil part 21 of the inner cylinder 15 on the outer side of the bend increases. As a result, the length of the central part of the inner cylinder 15 does not change even when bent, and the posture is stabilized.

At this time, the inner coil part 19 of the inner cylinder 15 is pushed out toward the outside of the bend. This extrusion of the inner coil part 19 is permitted by the increased pitches 21b between adjacent wound parts 21a of the outer coil part 21 of the inner cylinder 15 at the bent outer part. Therefore, the bending motion is able to be performed smoothly.

Moreover, during bending, the corresponding wound parts 19a of the inner coil part 19 continue to fit between the adjacent wound parts 21a of the outer coil part 21 of the inner cylinder 15.

Therefore, as in the straight state, the driving part 5 and the driven part 7 are prevented from being pushed inadvertently due to compression in the axial direction, and fluctuations in the length of the central part is able to be suppressed. Therefore, the driven part 7 linearly follows the bending of the driving part 5 and bends with good followability.

Effect of Example 1

As described above, this example includes the elastically bendable driving part 5, the elastically bendable driven part 7 provided apart from the driving part 5, and the linking part 9 that connects the driving part 5 and the driven part 7 and pulls and bends the driven part 7 according to bending of the driving part 5.

Each of the driving part 5 and the driven part 7 includes an inner coil part 19 and an outer coil part 21 that are bendable in the axial direction and the corresponding wound parts 19a of the inner coil part 19 are fitted into the pitches 21b between the adjacent wound parts 21a of the outer coil part 21.

Therefore, in this example, pushing of the driving part 5 and the driven part 7 in the axial direction is suppressed during bending and during non-bending before and after bending, and the followability of the driven part 7 to the driving part 5 is able to be improved, and enables intuitive operation.

Further, the linking part 9 is a drive wire 25 as a cord-like member that connects positions radially displaced from the center of the driving part 5 and the driven part 7, and when the bending operation mechanism 1 sets so that the bending angle of the driving part 5 is θ1, θ2 is the bending angle of the driven part 7, r1 is the amount of displacement of the drive wire 25 at the driving part and r2 is the amount of displacement of the drive wire 25 at the driven part 7, there is a relationship of θ1:θ2=r2:r1.

In this example, since pushing of the driving part 5 and the driven part 7 in the axial direction is suppressed, the relationship between the lengths L1 and L2 of the driving part 5 and the driven part 7 is maintained, and the θ1:θ2=r2:r1 relationship is able to be reliably obtained. Therefore, the bending angles θ1 and θ2 of the driving part 5 and the driven part 7 is able to be set accurately according to the amount of displacement of the drive wire 25.

In this example, the amounts of displacement r1 and r2 are set equal, and the bending angles θ1 and θ2 are set equal so the driven part 7 is able to be reliably bent by the amount of bending of the driving part 5, and a more intuitive operation becomes possible.

Example 2

(A) and (B) of FIG. 7 are schematic cross-sectional views of a bending operation mechanism according to example 2 of the invention, with (A) of FIG. 7 showing a normal state and (B) of FIG. 7 showing a bending state. FIG. 8 is a perspective view showing the state of the drive wire of the bending operation mechanism of FIG. 7. In addition, in Example 2, the same code is attached to the structure corresponding to example 1, and the repeated description is omitted.

In Example 2, the drive wires 25 as the respective cord-like members connect the driving part and the driven part 7 at positions different by 180 degrees in the circumferential direction. Others are the same as example 1.

That is, each drive wire 25 is provided so as to be gradually displaced in the circumferential direction so as to form a spiral shape, and is displaced from the connection position to the movable part 13 of the driving part 5 and the connection position to the movable part 13 of the driven part 7 by 180 degrees in the circumferential direction. The amount of displacement of the drive wire 25 is not limited to 180 degrees, but may be any other angle, and the driving part 5 and the driven part 7 may be connected at different positions in the circumferential direction according to this angle.

The drive wire 25 of this example is formed in a spiral shape within the shaft 3 that includes the driving part 5 and the driven part 7, and due to the spiral shape in the shaft 3, the drive wire 25 is displaced 180 degrees in the circumferential direction corresponding to the connection at positions different by 180 degrees. In other words, the drive wire 25 is not spiral but parallel in the driving part 5 and the driven part 7. However, the drive wire 25 may be configured in a spiral shape as a whole from the movable part 13 of the driving part 5 to the movable part 13 of the driven part 7.

In the shaft 3, a plurality of holding members or the like arranged in the axial direction are formed with holding holes that are gradually displaced in the circumferential direction, and the drive wire 25 is inserted through the holding hole to hold the spiral shape. The drive wire 25 is inserted through the driving part 5 and the driven part 7 in the same manner as in the example 1.

In example 2, the driven part 7 is able to be bent in the direction in which the driving part 5 is bent, and a more intuitive operation is able to be performed. Further, in this example, since the drive wire 25 is spiral only within the shaft 3, the structures of the driving part 5 and the driven part 7 are prevented from being complicated, the operation is stabilized, and versatility is improved. In addition, even in the example 2, the same effects as in the example 1 are able to be obtained.

Example 3

FIG. 9 is a schematic cross-sectional view showing a bending operation mechanism according to Example 3 of the present invention when bent. In addition, in Example 3, the same code is attached to the structure corresponding to Example 1, and the repeated description is omitted.

In the example 3, the length L1 from the connection position of the linking part 9 to the driving part 5 to the base part 11 as the base end part of the driving part 5 is longer than the length L2 from the connection position of the linking part 9 to the driven part 7 to the base part 11 as the base end part of the driven part 7. Others are the same as example 1.

In this example, the length of the driving part 5 is longer than the length of the driven part 7 in the axial direction, and the drive wire 25 of the linking part 9 is connected to the movable parts 13 of the driving part 5 and the driven part 7 as in example 1.

Note that the length L1 may be formed shorter than the length L2. In this case, the length of the driving part 5 is made shorter in the axial direction than the length of the driven part 7, and the drive wire 25 of the linking part 9 connects between the movable parts 13 of the driving part 5 and the driven part 7 as in example 1. Therefore, in this example, the length L1 may be different from the length L2.

In example 3, as in example 1, the bending angle θ1 of the driving part 5 and the bending angle θ2 of the driven part 7 are equal so the amount of displacement of the movable part 13 of the driving part 5 to reach the bending angle θ1 is larger than the amount of displacement of the movable part 13 of the driven part 7 to reach the bending angle θ2.

As a result, a small displacement of the movable part 13 of the driven part 7 is able to be controlled by a large displacement of the movable part 13 of the driving part 5. The delicate movement of the driven part 7 is made possible without reducing the size of the driving part 5, the operability of the delicate movement is able to be improved, and operation errors are able to be suppressed.

Conversely, if the length L1 is shorter than the length L2, a small displacement of the movable part 13 of the driving part 5 is able to control a large displacement of the movable part 13 of the driven part 7, and the driven part 7 can be caused to make a large displacement without increasing the size of the driving part 5.

In addition, this example is also able to achieve the same effects as example 2.

Example 4

FIG. 10 is a schematic cross-sectional view showing a bending operation mechanism according to example 4 of the invention when bent. In addition, in example 4, the same code is attached to the structure corresponding to example 2, and the repeated description is omitted.

In the example 4, the amount of displacement r1 of the drive wire 25 in the driving part 5 is made larger than the amount of displacement r2 of the drive wire 25 in the driven part 7. Others are the same as the example 1.

That is, the outer cylinder 17 of the driving part 5 has a larger diameter than the outer cylinder 17 of the driven part 7, and accordingly the insertion hole 23c of the driving part 5 is arranged radially outside the insertion hole 23c of the driven part 7. By inserting the drive wire 25 through the insertion hole 23c, the amount of displacement r1 is made larger than the amount of displacement r2.

Therefore, the bending angle θ1 of the driving part 5 is smaller than the bending angle θ2 of the driven part 7 from the relationship of θ1:θ2=r2:r1. Note that the amount of displacement r1 may be smaller than the amount of displacement r2.

In the example 4, it is possible to cause the driven part 7 to perform a bending operation with a large bending angle θ2 by the bending operation with a small bending angle θ1 of the driving part 5. Therefore, in this example, the driven part 7 is able to be greatly bent with a small operating force. Moreover, the diameter of the driving part 5 is able to be increased to facilitate operation, and bending is able to be performed with a smaller operating force.

Conversely, when the amount of displacement r1 is smaller than the amount of displacement r2, the bending operation with the large bending angle θ1 of the driving part 5 is able to cause the driven part 7 to perform the bending operation with the small bending angle θ2. Therefore, it is possible to perform delicate movements of the driven part 7, improve the operability of the delicate movements, and suppress operational errors.

In addition, even in the example 4, the same effect as the example 2 are able to be obtained.

Example 5

FIG. 11 is a schematic view showing the state of the drive wire of the bending operation mechanism according to example 5 of the invention. In addition, in example 4, the same code is attached to the structure corresponding to example 1, and the repeated description is omitted. In this example, three drive wires 25 are used. Others are the same as the example 1. The three drive wires 25 are arranged at predetermined intervals in the circumferential direction, and connect the driving part 5 and the driven part 7 at positions facing each other in the axial direction.

Even in the example 5, the same effects as in the example 1 are able to be obtained.

FIG. 12 is a schematic view showing a state of a drive wire of a bending operation mechanism according to a modification of the example 5. FIG. 13 is a conceptual view showing connection positions of drive wires of the bending operation mechanism of FIG. 12.

As a modification, in example 5, being the same as example 2, the drive wire 25 connects the driving part 5 and the driven part 7 at positions different by 180 degrees in the circumferential direction.

This modified example is able to achieve the same effects as the example 2.

What is claimed is:

1. A bending operation mechanism, comprising:
   a driving part that is elastically bendable;
   a driven part that is spaced apart from the driving part and is elastically bendable; and
   a linking part that connects between the driving part and the driven part and pulls and bends the driven part in response to bending of the driving part,
   wherein each of the driving part and the driven part comprises an inner coil spring and an outer coil spring that are bendable in an axial direction, and wound parts corresponding to the inner coil spring are fitted to gaps between adjacent wound parts of the outer coil spring,
   wherein a wound part of the inner coil spring contacts both adjacent wound parts of the outer coil spring, and a wound part of the outer coil spring contacts both adjacent wound parts of the inner coil spring,
   wherein the bending operation mechanism is configured such that when the linking part is pulled to bend the driven part, in the driven part, the gaps between the adjacent wound parts of the outer coil spring on an outer side of the bend increases, and the inner coil spring on the outer side of the bend is pushed out toward the outer side of the bend to fit in the increased gaps between the adjacent wound parts of the outer coil spring.

2. The bending operation mechanism according to claim 1, wherein a length from a connection position of the linking part to the driving part to a base end part of the driving part is different from a length from a connection position of the linking part to the driven part to a base end part of the driven part.

3. The bending operation mechanism according to claim 2, wherein the driving part and the driven part have different axial lengths, and the linking part connects between tip parts of the driving part and the driven part.

4. The bending operation mechanism according to claim 3, wherein the linking part is a cord-like member that connects positions radially displaced from centers of the driving part and the driven part, and
   in response to a bending angle of the driving part being $\theta 1$, a bending angle of the driven part being $\theta 2$, an amount of displacement of the cord-like member at the driving part being r1, and an amount of displacement of the cord-like member at the driven part being r2, a relationship of $\theta 1:\theta 2=r2:r1$ is established.

5. The bending operation mechanism according to claim 3, wherein the linking part comprises one or more cord-like members, and
   each cord-like member connects the driving part and the driven part at positions different by 180 degrees in a circumferential direction.

6. The bending operation mechanism according to claim 2, wherein the linking part is a cord-like member that connects positions radially displaced from centers of the driving part and the driven part, and
   in response to a bending angle of the driving part being $\theta 1$, a bending angle of the driven part being $\theta 2$, an amount of displacement of the cord-like member at the driving part being r1, and an amount of displacement of the cord-like member at the driven part being r2, a relationship of $\theta 1:\theta 2=r2:r1$ is established.

7. The bending operation mechanism according to claim 2, wherein the linking part comprises one or more cord-like members, and
   each cord-like member connects the driving part and the driven part at positions different by 180 degrees in a circumferential direction.

8. The bending operation mechanism according to claim 1, wherein the linking part is a cord-like member that connects positions radially displaced from centers of the driving part and the driven part, and
   in response to a bending angle of the driving part being $\theta 1$, a bending angle of the driven part being $\theta 2$, an amount of displacement of the cord-like member at the driving part being r1, and an amount of displacement of the cord-like member at the driven part being r2, a relationship of $\theta 1:\theta 2=r2:r1$ is established.

9. The bending operation mechanism according to claim 4, wherein the linking part comprises one or more cord-like members, and
   each cord-like member connects the driving part and the driven part at positions different by 180 degrees in a circumferential direction.

10. The bending operation mechanism according to claim 1, wherein the linking part comprises one or more cord-like members, and
    each cord-like member connects the driving part and the driven part at positions different by 180 degrees in a circumferential direction.

11. The bending operation mechanism according to claim 5, wherein each cord-like member is formed in a spiral shape between the driving part and the driven part, and is displaced 180 degrees corresponding to connection at the positions different by 180 degrees due to the spiral shape between the driving part and the driven part.

* * * * *